United States Patent [19]

Cummings et al.

[11] Patent Number: 4,909,999
[45] Date of Patent: Mar. 20, 1990

[54] FLOW-THROUGH VAPOR PHASE STERILIZATION SYSTEM

[75] Inventors: Arthur L. Cummings; Robert W. Childers; Thaddeus J. Mielnik, Jr., all of Erie, Pa.

[73] Assignee: American Sterilizer Company, Erie, Pa.

[21] Appl. No.: 323,187

[22] Filed: Mar. 13, 1989

Related U.S. Application Data

[63] Continuation of Ser. No. 70,271, Jul. 6, 1987, abandoned.

[51] Int. Cl.[4] ............ A61L 9/03; A61L 2/26
[52] U.S. Cl. ............... 422/298; 219/271; 422/30; 422/292; 422/294; 422/307
[58] Field of Search ......... 422/292, 294, 299, 302, 422/307, 29, 30, 174, 177, 900, 905; 219/271, 430, 439

[56] References Cited

U.S. PATENT DOCUMENTS

| | | | |
|---|---|---|---|
| 1,108,521 | 8/1914 | Scheuermann | 422/29 X |
| 1,912,209 | 5/1933 | Lassen et al. | 422/30 X |
| 1,932,122 | 10/1933 | Schulte | 422/299 X |
| 3,117,832 | 1/1964 | Thomas | 422/29 X |
| 3,245,250 | 4/1966 | Parks, Jr. | 219/271 |
| 3,443,884 | 9/1965 | Linder | 21/56 |
| 3,773,466 | 11/1973 | Linder | 21/94 |
| 3,851,436 | 12/1974 | Frase et al. | 422/29 |
| 3,912,451 | 10/1975 | Gaglia, Jr. | 21/58 |
| 3,926,107 | 12/1975 | Dunlap et al. | 422/29 X |
| 4,166,096 | 8/1979 | Gillis et al. | 422/299 |
| 4,169,123 | 9/1979 | Moore et al. | 422/29 |
| 4,169,124 | 9/1979 | Forstrom et al. | 422/33 |
| 4,261,950 | 4/1981 | Bainbridge et al. | 422/295 |
| 4,337,223 | 6/1982 | Kaye | 422/30 X |
| 4,435,194 | 3/1984 | Picard et al. | 422/29 X |
| 4,512,951 | 4/1985 | Koubek | 422/33 |
| 4,642,165 | 2/1987 | Bier | 203/12 |

FOREIGN PATENT DOCUMENTS

| | | | |
|---|---|---|---|
| 0022553 | 2/1984 | Japan | 422/30 |
| 2131695 | 6/1984 | Sweden | 422/298 |
| 1574488 | 9/1980 | United Kingdom | |
| 1582060 | 12/1980 | United Kingdom | |

OTHER PUBLICATIONS

Kohler et al., "Catalytic Decomposition of Hydrogen Peroxide by Manganese Alumina", NTIS Document PB 80-124274, National Science Foundation, Washington, DC (1974).
Selected pages from Disinfection, Sterilization, and Preservation (S. S. Block 2d ed. 1977).

*Primary Examiner*—Barry S. Richman
*Assistant Examiner*—Amalia L. Santiago
*Attorney, Agent, or Firm*—Kirkpatrick & Lockhart

[57] ABSTRACT

The present invention provides a flow-through system for use with at least one sealable pressure or nonpressure container. The system can be used to selectively sterilize, humidify and aerate the container and can be integrally or releasably attached to the container. The system includes at least one liquid reservoir for holding a sterilant, such as an aqueous solution of hydrogen peroxide. A second liquid reservoir for holding water for humidification may be provided. The system also includes a unit which houses a heater for vaporizing incoming liquid and optionally heating incoming air and a converter for converting selected vapors to a form suitable for disposal. A vacuum motor draws air from the container to reduce pressure therein so that air from an air supply is drawn through an air filter into the heater and into the container. A substantial portion of the withdrawn air from the container is diverted to the converter. The reduced pressure in the container may be sufficient for urging liquid from the reservoir to the heater where the liquid is vaporized and carried by the stream of air into the container. Alternatively, a remaining portion of withdrawn air may be used to exert pressure within the liquid reservoir to urge the liquid to the heater. Valves are provided to selectively control liquid flow to the heater.

13 Claims, 3 Drawing Sheets

FLOW-THROUGH VAPOR PHASE STERILIZATION SYSTEM

This is a continuation of co-pending application Ser. No. 07/070,271 filed on July 6, 1987, now abandoned.

BACKGROUND OF THE INVENTION

1. Field of the Invention

The present invention relates to sterilization systems and, more particularly, to vapor phase sterilization systems.

2. Description of the Prior Art

There is often a need to sterilize the interior of a container or a room due to some unexpected contamination or to prepare the container or room for a special use. For example, clean rooms are needed to manufacture certain kinds of microelectronic products and pharmaceuticals. The room must be periodically sterilized. The interior of incubators may require sterilization to rid them of pathogenic contaminants. In addition, laboratory spills of highly contagious substances may unexpectedly contaminate an area. Such containers and their contents are not easily sterilized by conventional methods.

Gaseous sterilization systems, such as ethylene oxide, formaldehyde, ozone and hydrogen peroxide, have bee used with varying success in a variety of applications. One problem with each of these sterilants is disposing of the residual vapors following sterilization. See DISINFECTION, STERILIZATION, AND PRESERVATION, 592, 677 (S.S. Block 2d ed. 1977).

Conventional gaseous/steam sterilization systems use vacuum pumps to evacuate chambers prior to introduction of the sterilant. Air blowers and injection pumps, or a vacuum source and gravity feed injection system are also commonly used in such sterilization systems. Due to the extreme pressure differentials required, vacuum or pressure systems require the use of sturdy, rigorously sealed vacuum/pressure vessels.

One arrangement for a steam-heated autoclave is disclosed by Linder U.S. Pat. No. 3,773,466, which issued on November 20, 1973. The system described by Linder includes an autoclave, a heating chamber for generating steam, a water tank and a steam trap. Steam entering the autoclave forces air out to the steam trap and to the water tank. At the end of the cycle, steam flows from the autoclave, back through the heating chamber through a three-way valve to the water tank. When pressure within the system is equalized, water flows by gravity from the water tank to the heating chamber for use in subsequent cycles. A related system is disclosed in Linder U.S. Pat. No. 3,443,884.

Moore et al. U.S. Pat. No. 4,169,123, and Forstrom et al. U.S. Pat. No. 4,169,124, both of which issued on Sept. 25, 1979, disclose methods of "cold" gas sterilization using hydrogen peroxide gas at temperatures below 80° C. Moore recommends that liquid hydrogen peroxide should be volatilized within the sterilization chamber but indicates also that the volatilization may occur outside of the chamber. The hydrogen peroxide vapor may then be introduced into the sterilization chamber by air displacement. Moore provides no details as to how the introduction of the vapors by air displacement is to be achieved.

Bier U.S. Pat. No. 4,642,165, which issued on Feb. 10, 1987, discloses a method of vaporizing successive increments of a multicomponent liquid, such as an aqueous solution of hydrogen peroxide, for injection into a vacuum chamber. The vacuum in the chamber draws the multicomponent vapor into the chamber.

Koubek U.S. Pat. No. 4,512,951, which issued on Apr. 23, 1985, discloses a method of liquid-contact hydrogen peroxide sterilization. Goods to be sterilized are maintained in the sterilization chamber at a temperature below the dew point of the vapor sterilant. An aqueous solution of hydrogen peroxide is vaporized and passed into the evacuated sterilization chamber where, upon contact with the goods, the vapor condenses to form a liquid layer of sterilant on the goods. The vacuum in the chamber draws the vapor in.

United Kingdom Patent No. 1,582,060, issued to Tetra Pak International, discloses a similar liquid contact hydrogen peroxide sterilization method operated without a vacuum chamber. Liquid hydrogen peroxide is pumped to an ultrasonic spray nozzle which is operated by a stream of dehydrated air. A mist of hydrogen peroxide is sprayed into a container and mixed with hot air to change the mist into a vapor. The vapor is piped into a nonpressurized sterilization chamber where it condenses on a cool, moving web of material. A stream of hot air in an adjacent chamber removes the hydrogen peroxide layer from the web. The stream is then passed to a water separator where it is relieved of the sterilant.

United Kingdom Patent No. 1,574,488 also discloses a method for removing liquid hydrogen peroxide by means of a hot air stream.

Hydrogen peroxide, although irritating to the skin and eyes, decomposes to water and oxygen. A variety of materials are known which catalytically decompose hydrogen peroxide upon contact. Exotic metal catalysts, such as platinum black, have been evaluated as described in Gaglia, Jr. U.S. Pat. No. 3,912,451, issued on Oct. 14, 1975, for use in removing hydrogen peroxide from contact lenses.

The use of manganese dioxide ($MnO_2$) supported on alumina in a continuous, tubular, packed bed reactor was evaluated for the catalytic decomposition of hydrogen peroxide by Kohler et al. "Catalytic Decomposition of Hydrogen Peroxide by ManganaseAlumina", NTIS Document PB 80-124274, National Science Foundation, Washington, DC (1974). The $MnO_2$ does not completely destroy incoming hydrogen peroxide. A second treatment stage employing immobilized catalase is used to destroy any residual hydrogen peroxide.

Other materials which are known to catalyze hydrogen peroxide are metals, such as lead, iron, copper, cobalt, silver, gold and palladium. Houlsby U.S. Pat. No. 4,521,375 discloses the use of pyruvic acid and salts thereof to destroy hydrogen peroxide. It is also known that heat will lead to the decomposition of hydrogen peroxide.

There is a need for a simple, inexpensive system, preferably in modular form, for use with existing nonpressure or pressure containers or vessels, to generate a sterilant vapor, deliver it to the area to be sterilized and then dispose of the residual vapors.

SUMMARY OF THE INVENTION

The present invention provides a vapor flow-through system which can be integrally associated with sealable containers or which can be a modular unit adapted for releasable connection to a variety of existing pressure or nonpressure sealable containers. The system can be used with at least one sealable container such as an incubator, a refrigerator, a clean room or any sealable enclosure. The modular system includes at least one liquid reservoir fluidly connected to the container, means fluidly connected to the inlet of the container for heating liquid from the reservoir to a temperature sufficient for substantially instantaneously transforming liquid into vapor, valve means for selectively controlling flow from the reservoir to the heating means, air intake means fluidly connected to the heating means, means fluidly connected to the outlet of the container for converting selected vapor into a form suitable for disposal, and means for withdrawing air and vapor from the outlet of the container wherein a substantial portion of air and vapor so withdrawn is directed to the converting means and a pressure differential between the reservoir and the heating means is created to urge liquid from the reservoir to the heating means when the valve means is open. The withdrawal of air from the container reduces pressure within the container sufficient to draw a stream of air from the air intake means through the heating means where the stream of air carries vapor formed in the heating means into the container.

Fluid connecting means define a flow-through path from the intake means, through the heating means, into and through the container and past the withdrawing means to a first connection directed to the converting means. A second connection is preferably directed to the reservoir. The second connection continues from the reservoir, through the valve means to the heating means where the second connection merges with the path from the heating means to the container.

The second connection leading to the reservoir, when employed, is preferably more narrow than the first connection to the converting means so that a substantial portion of air or vapor withdrawn from the container is directed to the converting means. The remaining portion of air or vapor would then be directed along the narrow second connection to the reservoir to create a pressure differential between the reservoir and the heating means to urge the liquid toward the heating means.

The system may further include a three-way valve disposed along the first connection for selectively directing flow from the container to the converting means for disposal or to the heating means for recirculation.

There may be two liquid reservoirs, one preferably holding a sterilant, such as an aqueous solution of hydrogen peroxide in suitable concentrations, and the other holding water. The dual reservoir system can be selectively used for sterilization, or alternatively, for humidification within the container. Each liquid reservoir has associated therewith one valve means for controlling delivery of liquid to the heating means. When both valve means are closed, the system can be used for aeration within the container.

When two containers are used, the system further includes an intake three-way valve disposed between the heating means and the containers for selectively directing flow to one or the other container, and an outtake three-way valve disposed between the two containers and the withdrawing means for selectively controlling flow from each container.

The heating means and converting means are preferably housed in a single unit which includes an inner housing defining an inner chamber and an outer housing surrounding the inner housing to define therebetween an outer chamber. The inner chamber has at least one inlet and an outlet and the outer chamber has an inlet and an outlet.

Means, such as metallic spheres having surfaces for catalytically degrading selected vapor, are disposed within the outer chamber. The degrading means provide sufficient contact with incoming vapor to promote substantially complete degradation. The unit also includes a heater for providing sufficient heat to the outer chamber to enhance degradation of incoming vapor and for providing sufficient heat to the inner chamber to substantially instantaneously transform incoming liquid into vapor.

BRIEF DESCRIPTION OF THE DRAWINGS

The present invention will be better understood by reference to the drawings in which.

Figure 2:
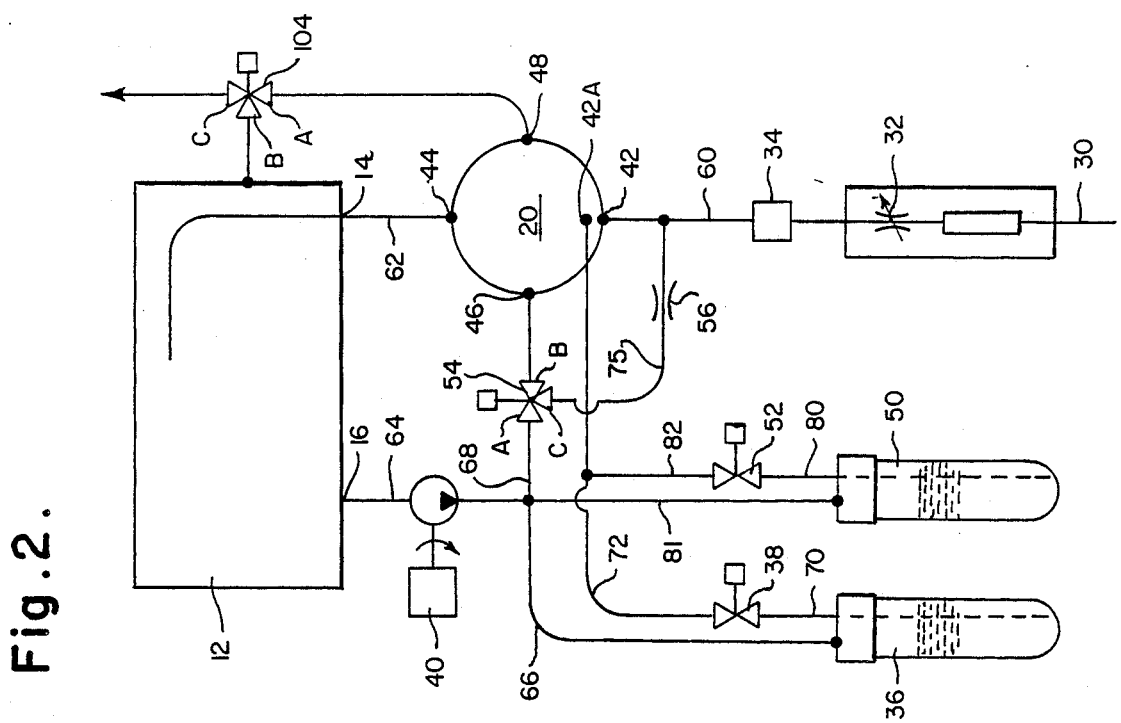
FIG. 2 is a schematic illustration of an alternative embodiment of the system of FIG. 1 with dual liquid reservoirs.

DETAILED DESCRIPTION OF THE PREFERRED EMBODIMENT

FIGS. 1 through 6 illustrate the preferred embodiments of the sterilization system of the present invention and equipment for use in such a system. The sterilization system can be housed in modules for releasable or permanent attachment to sealable containers 12. The containers 12 need not be pressure/vacuum vessels and can, therefore, be of weaker construction relative to a typical pressure/vacuum vessel. Any relatively rigid, sealed structure, including, but not limited to, a room, an incubator, a refrigerator or a tent with a rigid frame for placement over an area or a device to be sterilized can provide the container 12 for use with the sterilization system of the present invention.

Referring to FIG. 1, the sterilization system, in its simplest form, includes a vaporizer/converter 20, an air intake 30, an air flow meter 32, air filter 34, liquid sterilant reservoir 36, injection valve 38 and vacuum motor 40. The container 12 has an inlet 14 for air and vapor entry and an outlet 16 for air and vapor withdrawal.

The vaporizer and converter may be two separate units appropriately connected within the system. In the preferred embodiment, however, they are used together as a single unit. The vaporizer/converter 20 is shown in greater detail in FIGS. 5 and 6. Vaporizer/converter 20 has an external housing 22 and an internal housing 24. An outer chamber 26 is defined therebetween. The internal housing 24 defines an inner chamber 28. The outer chamber 26, which functions as the converter, houses a plurality of spheres 58 which define a low flow-resistant tortuous path having a high surface area for degradation of the sterilant. When the system is used as a hydrogen peroxide sterilization system, the metallic spheres 58 are preferably coated, or made entirely of, copper or some other material known to catalytically degrade hydrogen peroxide. A heating element 84, such as an electric band heater, provides temperatures sufficiently high within the outer chamber 26, which, when coupled with the highly catalytic, high surface area tortuous pathway created by spheres 58, nearly instantaneously catalytically decomposes the sterilant vapor. Although the spheres 58 have been demonstrated to work well in decomposing hydrogen peroxide into water and oxygen, any suitable environment which completely converts a particular sterilant to a form suitable for disposal will suffice.

Heat from heater 84 and, to some extent, the heat given off during the decomposition of the sterilant, is conducted through the spheres 58 and internal housing 24 to inner chamber 28, which functions as the vaporizer to instantaneously vaporize the liquid sterilant when it enters the inner chamber 28 of vaporizer/converter 20. The vaporizer temperature when used for hydrogen peroxide sterilization is about 60-150° C. (140-302° F.). The vapor is then passed into the container 12 as described more fully below. The vapor may pass into the container 12 continually or may pass incrementally as disclosed in Bier U.S. Pat. No. 4,642,165, the relevant portions of which are hereby incorporated herein by reference.

Vacuum motor 40 can be any suitable known motor. The fluid connections between the components of the system may be any suitable known conduits, piping or similar connecting means.

In operation, vacuum motor 40 is turned on. Container 12 should be sealed. The force of vacuum motor 40 draws air from the container 12. The vacuum level within container 12 is preferably kept low by vacuum motor 40 to about one to ten inch water column, which is about 0.036-0.36 psi. As the pressure within container 12 decreases, vacuum motor 40 ultimately draws air from air intake 30 through flow meter 32 and air filter 34 along a suitable path 60 through portal 42 into the inner chamber 28 of vaporizer/converter 20 where the air may be optionally heated, then is drawn out through portal 44 along path 62 and into container 12 through entryway 14. The change in temperature of the air stream upon passage through chamber 28 depends on the air flow rate and the temperature differential between the incoming air and the chamber surfaces. As the vacuum motor 40 continues to operate, the air drawn through vaporizer/converter 20 into container 12 flows through container 12 and out through exit 16 along path 64 past vacuum motor 40.

The air stream is preferably split between paths 66 and 68. Path 66 is preferably narrower than path 68 so that a substantial portion of the stream of air flows along path 68 to portal 46 into outer chamber 26 of vaporizer/converter 20 and out portal 48 to exhaust. A remaining portion of air flows along path 66 and is sufficient when combined with reduced pressure in chamber 28 to create a pressure gradient across reservoir 36 to force liquid sterilant through path 70. In an alternative embodiment (not shown), path 66 may be eliminated. Suction from container 12, through vaporizer/converter 20 draws liquid into chamber 28, as described below.

If injection valve 38 is open, liquid sterilant will flow along path 72 through portal 42A into chamber 28 of vaporizer/converter 20 where the liquid sterilant will be vaporized upon contact with the heated surface of inner chamber 28. The resulting vapor is then carried by the air stream created by vacuum motor 40 through portal 44 along path 62 through entryway 14 into container 12. Any contamination introduced by the air itself which is not removed by air filter 34 will be sterilized upon exposure to the sterilant vapor.

The flow of vapor phase sterilant through container 12 continues for a time period suitable for sterilizing the interior of container 12 and/or its contents. The system of the present invention employs suitable known sterilization cycles. Depending on the container contents, the simultaneous flow of air may create sufficient turbulence to mix the vapor phase sterilant throughout container 12. Additional or alternative means for creating turbulence, such as fans, may be provided. In the preferred embodiment, wherein the container 12 is an incubator, approximately 6.5 ft$^3$ in volume, and the sterilant is hydrogen peroxide, the rate of flow for hydrogen peroxide sterilization is about 2.5 ft$^3$/min. The optimum rate of flow may vary depending on the size of the container and the cycle time for effective sterilization.

The vapor phase sterilant is withdrawn from container 12 through exit 16 along paths 64 and 68 through portal 46 into outer chamber 26 where, by virtue of the catalytic effect of spheres 58, the sterilant is degraded and exhausted through portal 48. When vapor phase hydrogen peroxide or ozone are used as the sterilant, the degraded components are harmless and can be vented to the atmosphere. When other gases, such as perhaps ethylene oxide or formaldehyde are used as the sterilant, and adequate means for destroying harmful gases do not fit within outer chamber 26, the exhaust must be contained and treated according to suitable known methods.

When no further sterilant entry into container 12 is required, the injection valve 38 is closed. Vacuum motor 40 continues for a period sufficient to permit the air stream to carry residual sterilant from container 12 to outer chamber 26 for degradation.

The sterilization system of the present invention is failsafe in that it will not permit injection of liquid sterilant into vaporizer/converter 20 when the container 12 is opened because the pressure differential across the reservoir 36 would be insufficient to urge the liquid from reservoir 36 into chamber 28 of vaporizer/converter 20. With the door open, no suction would be created to draw vapor to chamber 28 and there would be no air flow through chamber 28 to carry the vapor into container 12. Furthermore, the slight suction within container 12 prevents container 12 from being opened during operation. Complicated interlocking systems for container 12 can be avoided. Some prior art systems, in contrast, placed a blower on the upstream side of the sterilization chamber to push the vapor into the chamber. Such systems require interlocks on the chamber doors.

The slight suction created by vacuum motor 40 is substantially different from the degree of vacuum found in conventional vacuum sterilization systems. Vacuum motor 40, therefore, can be smaller than the vacuum pumps required to pull a significant vacuum within conventional vacuum sterilizers. In addition, due to the pressure gradient across reservoir 36, a pump is not needed to meter the flow of sterilant through injection valve 38. A relatively inexpensive injection valve 38 can, therefore, be used in the system. Any suitable known injection valve 38 for selectively metering and controlling the flow of liquid will suffice. The flow-through system of the present invention can provide a relatively low cost module for use with a variety of containers not heretofore suitable as sterilization chambers. The fluid connections of the module can be releasably attached to a container at an inlet and outlet of the container and sealed by suitable known connecting and sealing means, such as pipes, washers, gaskets, clamps and similar known devices.

Figure 1:
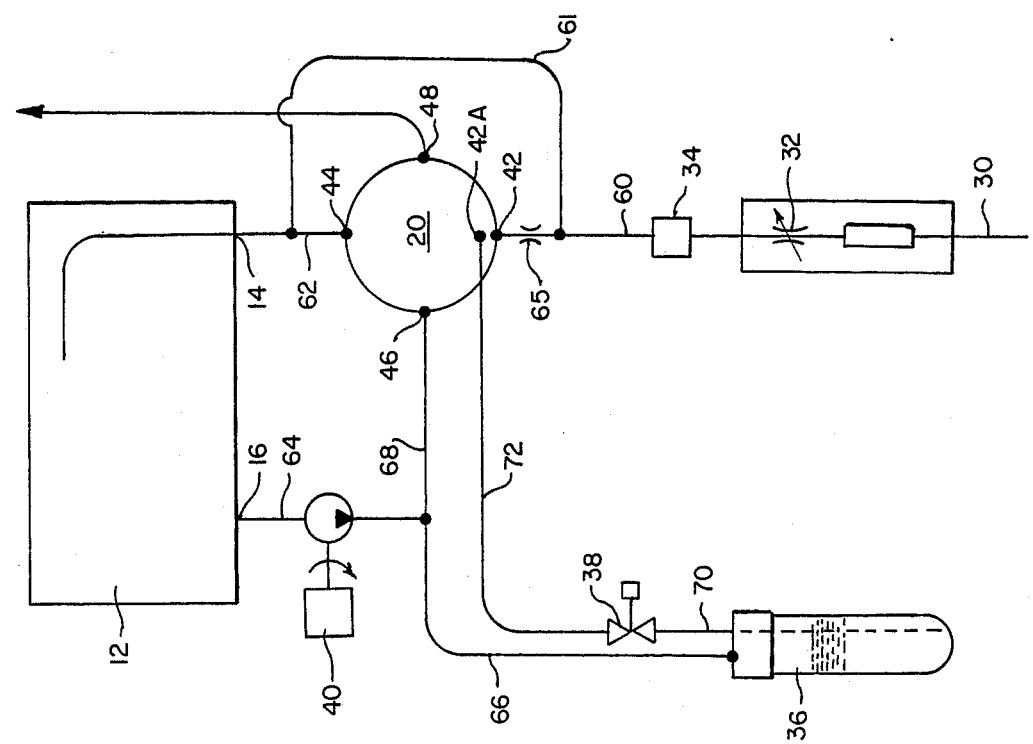
FIG. 1 is a schematic illustration of one embodiment of the flow-through system of the present invention.

An optional feature, shown in FIG. 1, is parallel path 61 and flow restrictor 65. Parallel path 61 permits some of the air from air intake 30 to bypass chamber 28. The remainder of the air flows through chamber 28. The air diverted along parallel path 61 joins the air or air/vapor mixture exiting chamber 28 and cools it. Flow restrictor 65, which is preferably a drilled orifice in path 60 having a smaller diameter than the diameter of path 61, can be used to divert most of the air along path 61. Alternatively, path 61 may have a flow restrictor so that most of the air enters chamber 28. The temperature of the air or air/vapor mixture entering container 12 can be controlled by adjusting the relative sizes of the orifices and paths 60, 61 and 65. Use of a parallel path 61 to cool air or the air/vapor mixture entering container 12 permits the use of greater heat in chamber 26 to provide a higher efficiency breakdown of sterilant vapor while still controlling the temperature going into the container 12.

An alternative embodiment of the sterilization system of the present invention is shown in FIG. 2. A second liquid reservoir 50 and injector valve 52 with appropriate pathways 80, 81 and 82 are added. In addition, a three-way diverter valve 54 is placed along path 68. An additional path 75 and a flow restrictor 56 lead from the diverter valve 54 to path 60 just before portal 42 into inner chamber 28 of vaporizer/converter 20.

The second reservoir 50 can hold water, for example, to humidify the air stream and container 12, if desired. When injector valve 52 is opened, injector valve 38 associated with reservoir 36 is closed. Similarly, when injector valve 38 is open, injector valve 52 is closed. The two liquid reservoirs, 36 and 50, are not ordinarily operated simultaneously, but, either may be operated whether diverter valve 54 is in position A→B or A→C.

When diverter valve 54 is open from A→B along path 68, the valve path A→C to path 75 is closed and air flow is the same as in FIG. 1 as explained above. When A→C is open, the valve path A→B is closed. The path A→C through diverter valve 54 along path 75 is used when air and/or vapor is to be recirculated through container 12 and not exhausted. The flow restrictor 56, which may be merely a drilled orifice along path 75, creates a pressure differential in the system. Path 75, due to flow restrictor 56 and the force of vacuum motor 40, is at a positive pressure relative to path 60 and container 12 is at a negative pressure relative to path 60. The air stream flows along path 75 toward portal 42 into vaporizer/converter 20. Back flow of air out of the air intake 30 is prevented by flow meter 32.

Humidification of container 12 is achieved by opening valve 52 and operating vacuum motor 40 as described above to urge water from reservoir 50 to chamber 28 where the water is vaporized and carried by an air stream through container 12. When sufficient water vapor has been formed in the system, valve 52 is closed. Diverter valve path A→C is open to direct the flow of water vapor and air withdrawn from container 12 through path 75 into chamber 28 for recirculation through container 12. When the water vapor needs to be replenished, valve 52 is opened for a suitable time. The pressure gradient created by flow restrictor 56 is sufficient, with the aid of vacuum motor 40, to recirculate the water vapor and air.

Aeration is achieved by closing valves 38 and 52 and opening path A→B of diverter valve 54, thereby supplying a continuous fresh stream of air to container 12. Alternatively, as illustrated in FIG. 2, a diverter valve 104 can be placed on the exhaust line exiting chamber 26. The air stream can pass through the converter to degrade any residual sterilant, then exit portal 48 and pass back into container 12 through valve path A→B. The already sterilized air is thereby recirculated through the system.

When container 12 is an incubator, the humid air flow offered by liquid reservoir 50 permits elimination of the water pan typically used to provide moisture for incubators. Water pans are known to provide a site for bacterial growth. In addition, the humidification provided by the flow-through system is significantly faster than the humidification obtained from use of a water pan which relies on natural evaporation. Furthermore, every time the incubator door is opened, the humidity within container 12 falls. Natural make up time can be about 8-12 hours. Humidification by the system of the present invention is about one-half hour.

Figure 3:
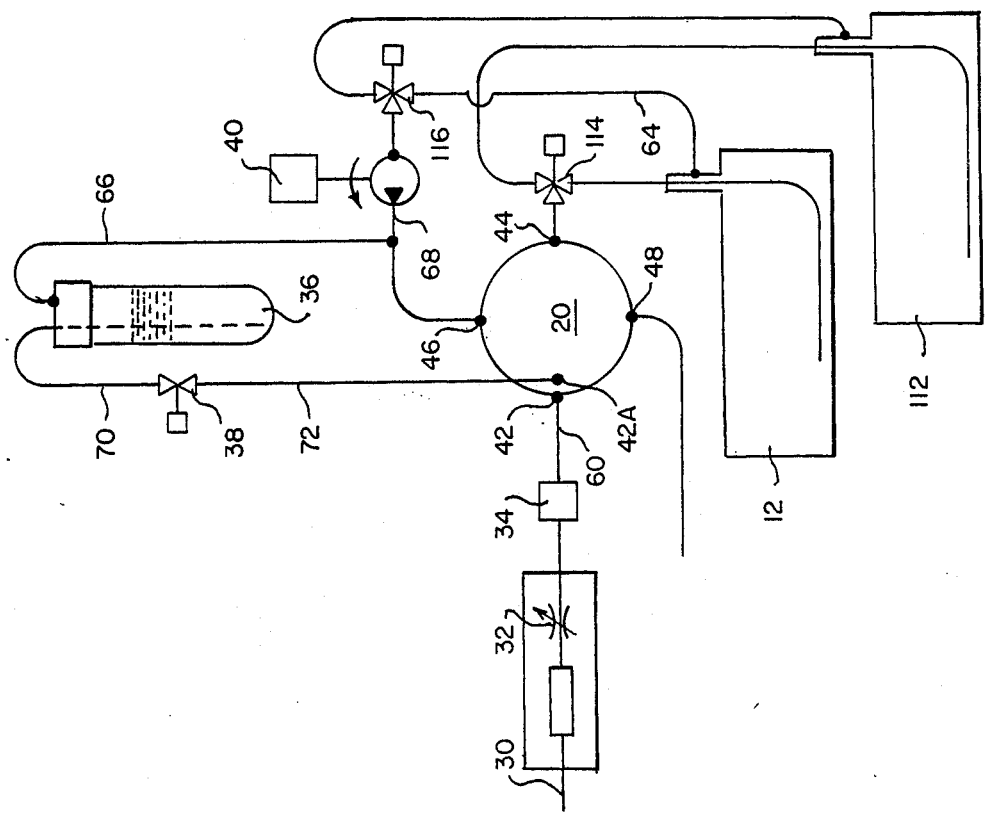
FIG. 3 is a schematic illustration of a third embodiment of the system shown in FIG. 1 with dual containers.
Figure 5:
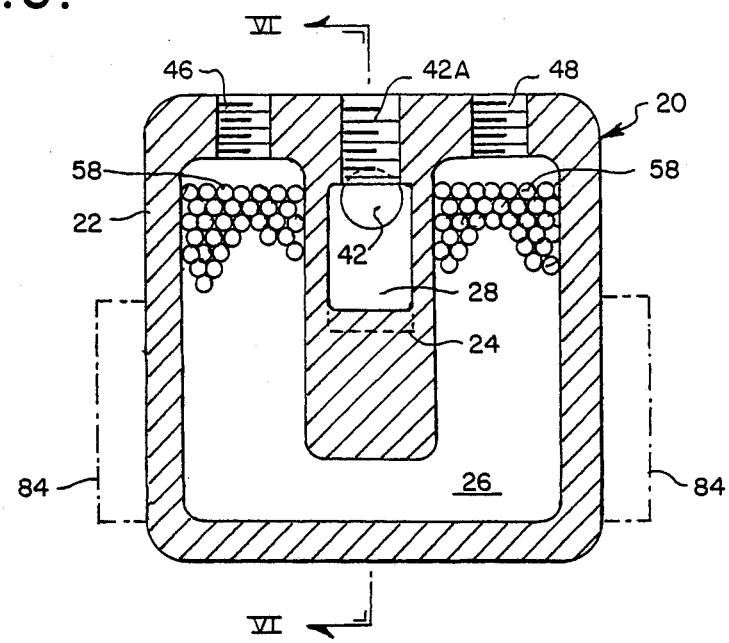
FIG. 5 is a section view of the vaporizer/converter used in the system of the present invention.
Figure 6:
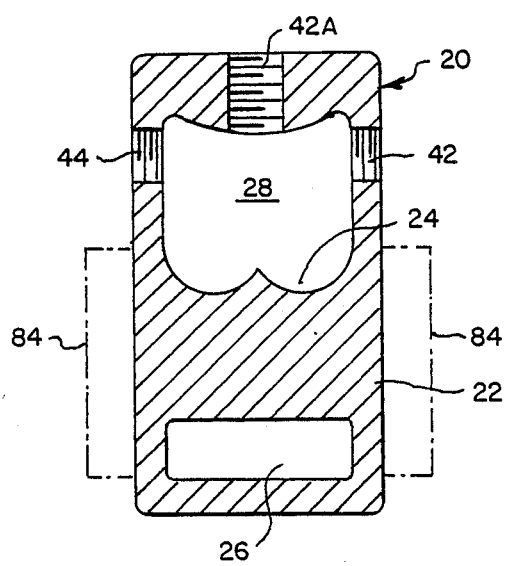
FIG. 6 is a section view of the vaporizer/converter of FIG. 5 along the line VI—VI.

A third embodiment of the flow-through system of the present invention is illustrated schematically in FIG. 3. A "time-share" system having dual sterilization containers 12 and 112 is provided. Three-way diverter valves 114 and 116 of a known variety control the flow of air and vapor into and out of containers 12 and 112. This embodiment of the system operates in the same manner as described above with the exception of the additional selective operation of valves 114 and 116 required to control flow to and from the desired container.

Figure 4:
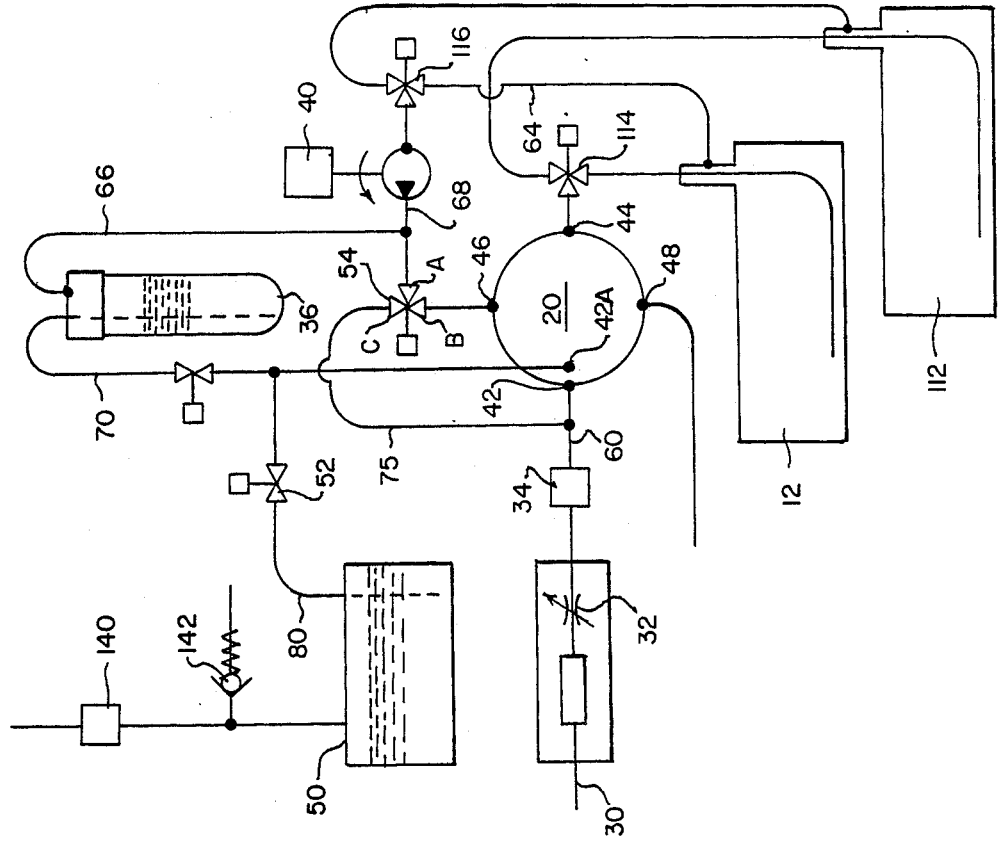
FIG. 4 is a schematic illustration of a fourth embodiment of the system shown in FIGS. 2 and 3 with dual liquid reservoirs and dual containers.

A fourth embodiment, illustrated schematically in FIG. 4, combines the dual container system of FIG. 3 with the dual liquid reservoir system of FIG. 2, with the exception that an extra air pump 140 and a solenoid valve 142 of a known variety are added to force liquid from reservoir 50 toward vaporizer/converter 20. This embodiment of the system operates in the same fashion as the embodiments described above except that, when the second liquid reservoir 50 is used, valve 38 is closed and pump 140 and solenoid valve 142 are activated.

What is claimed is:

1. A vapor flow-through system comprising:
   at least one sealable container having an inlet end an outlet;
   at least one liquid reservoir;
   an inner housing defining an inner chamber, said inner chamber having at least one first inlet fluidly connected to said at least one reservoir and a first outlet;
   an outer housing surrounding said inner housing to define therebetween an outer chamber, said outer chamber having a second inlet fluidly connected to said outlet of said at least one sealable container and a second outlet;
   means within said outer chamber for converting a selected vapor to a form suitable for disposal, said converting means providing sufficient contact with incoming vapor to promote substantially complete conversion;
   heating means for providing sufficient heat to said outer chamber to enhance conversion of incoming vapor and for providing sufficient heat to said inner chamber to substantially instantaneouly transform incoming liquid into vapor;

means connecting said heating means to said outer housing;

valve means respectively disposed between said each of least one reservoir and said inner chamber;

air intake means fluidly connected to said inner chamber;

means proximate said outlet of said at least one sealable container for continuously withdrawing air and vapor from said at least one seal container during operation of the system; and fluid connecting means having a first connection defining a flow-through path from said air intake means through said inner chamber, into and through said at least one sealable container, past said withdrawing means to said outer chamber, and a second connection from said at least one reservoir, through said valve means to said inner chamber where said second connection merges with said first connection and said flow-through path in said inner chamber to said at least one sealable container;

wherein said withdrawing means withdraws air from said at least one sealable container to reduce pressure therein sufficient to draw a stream of air through said flow-through path, and creates a pressure differential between said at least one reservoir and said inner chamber sufficient to urge liquid from said at least one reservoir, when said valve means is open, along said first connection to said inner chamber where vapor formed therefrom is carried by said stream of air along said flow-through path into said at least one sealable container.

2. The system of claim 1 wherein said at least one reservoir comprises two liquid reservoirs, each having associated therewith a valve means disposed between the reservoir with which said valve means is associated and said inner chamber, for controlling delivery of liquid to said inner chamber, and each said reservoir being fluidly connected through said inner chamber to said at least one sealable container.

3. The system of claim 1 further comprising a three-way valve for selectively directing flow from said at least one sealable container to said converting means for disposal or to said inner chamber for recirculation.

4. The system of claim 1 wherein said vapor is hydrogen peroxide and said converting means is a plurality of metallic spheres having outer surfaces made of material for catalytically degrading hydrogen peroxide.

5. The system of claim 1 further comprising an air filter and an air flow meter between said air intake means and said inner chamber.

6. The system of claim 1 wherein said at least one reservoir comprises two containers and said system further comprises:

an intake three-way valve disposed between said inner chamber and said two sealable containers for selectively directing flow to one sealable container or to the other sealable container; and an outtake three-way valve disposed between said two containers and said withdrawing means for selectively controlling flow from each said sealable container.

7. The system of claim 6 wherein said at least one reservoir comprises two liquid reservoirs, one said reservoir having associated therewith pumping means for exerting pressure within such one reservoir sufficient for urging liquid therefrom, when said associated valve means is opened, to said inner chamber.

8. The system of claim 1 further comprising:

means for diverting at least a portion of air flow around said inner chamber and for merging such diverted air flow with fluid exiting said inner chamber between said inner chamber and said at least one sealable container to reduce the temperature of such fluids.

9. The system of claim 8 wherein said diverting means is a bypass conduit having an inlet side disposed between said air intake and said inner chamber and an outlet side disposed between said inner chamber and said container, said system further comprising a flow restrictor to control the relative portions of air flow entering said bypass conduit and said inner chamber.

10. The system of claim 1 wherein said first connection is split after passing said withdrawing means into a third connection directed to said at least one reservoir.

11. The system of claim 1 further comprising valve means for selectively directing the flow from said outer chamber to said at least one sealable container to recirculate fluids in the system or to exhaust.

12. Apparatus for use with a vapor system comprising:

an inner housing defining an inner chamber, said inner chamber having at least one first inlet and a first outlet;

an outer housing surrounding said inner housing to define therebetween an outer chamber, said outer chamber having a second inlet and a second outlet;

a plurality of metallic spheres within said outer chamber, at least the surfaces of said spheres being made of a material which catalytically degrades selected vapor to a form suitable for disposal, said spheres providing sufficient contact with incoming vapor to promote substantially complete degradation;

heating means for providing sufficient heat to said outer chamber to enhance degradation of incoming vapor and for providing sufficient heat to said inner chamber to substantially instantaneously transform incoming liquid into vapor; and means for connecting said heating means to said outer housing.

13. The apparatus of claim 12 wherein said heating means is an electric heater connected to said outer housing and wherein heat from said electric heater and from the degradation of vapor is conducted through said metallic spheres to said inner housing.

* * * * *

UNITED STATES PATENT AND TRADEMARK OFFICE
CERTIFICATE OF CORRECTION

PATENT NO. : 4,909,999

DATED : March 20, 1990

INVENTOR(S) : Arthur L. Cummings et al.

It is certified that error appears in the above-identified patent and that said Letters Patent is hereby corrected as shown below:

Col. 1, line 27, delete "bee" and substitute therefor --been--.

Signed and Sealed this

Twenty-first Day of April, 1992

Attest:

HARRY F. MANBECK, JR.

*Attesting Officer*   *Commissioner of Patents and Trademarks*